US008178343B2

United States Patent
Lin et al.

(10) Patent No.: US 8,178,343 B2
(45) Date of Patent: May 15, 2012

(54) GENE CLUSTER DIAGNOSIS APPARATUS

(75) Inventors: Shiu-Ru Lin, Kaohsiung (TW); Hui-Jen Chang, Kaohsiung County (TW); Der-An Tsao, Kaohsiung (TW)

(73) Assignee: Fooyin University Hospital, Pingtung County (TW)

( * ) Notice: Subject to any disclaimer, the term of this patent is extended or adjusted under 35 U.S.C. 154(b) by 57 days.

(21) Appl. No.: 12/852,652

(22) Filed: Aug. 9, 2010

(65) Prior Publication Data

US 2011/0281774 A1 Nov. 17, 2011

(30) Foreign Application Priority Data

May 13, 2010 (TW) ................................. 99115357 A (51) Int. Cl.
*C12M 1/34* (2006.01)
*C12M 3/00* (2006.01)

(52) U.S. Cl. ...................... 435/287.2; 435/287.1; 506/39
(58) Field of Classification Search ................ 506/39
See application file for complete search history.

(56) References Cited

U.S. PATENT DOCUMENTS

2002/0022226 A1* 2/2002 Nakao et al. ...................... 435/6
2003/0175782 A1* 9/2003 Fukushima et al. ............... 435/6
2006/0068396 A1* 3/2006 Lin et al. ........................... 435/6

* cited by examiner

*Primary Examiner* — Michael Marcheschi
*Assistant Examiner* — Shanta G Doe
(74) *Attorney, Agent, or Firm* — Jackson IPG PLLC; Demian K. Jackson (57) ABSTRACT

A diagnosis apparatus is provided. A gene chip having a target gene cluster is used with the apparatus. The target gene cluster comprises a plurality of target genes related to a cancer. Thus, a fast, accurate, sensitive and cheap WEnCA-Chipball platform is provided for mass analysis and automatic operation while human error and time for diagnosis are both reduced.

9 Claims, 7 Drawing Sheets

FIG.1

| ATP2A2 | ATP6V0B | BMPR2 | CALM2 | CEBPB | CLSTN1 | COL4A1 | CXCL11 |
|--------|---------|-------|-------|-------|--------|--------|--------|
| ATP2A2 | ATP6V0B | BMPR2 | CALM2 | CEBPB | CLSTN1 | COL4A1 | CXCL11 |
| ATP2A2 | ATP6V0B | BMPR2 | CALM2 | CEBPB | CLSTN1 | COL4A1 | CXCL11 |
| CXCR4 | CYR61 | DVL3 | E2F4 | ETS1 | H2AFZ | L1CAM | LRP1 |
| CXCR4 | CYR61 | DVL3 | E2F4 | ETS1 | H2AFZ | L1CAM | LRP1 |
| CXCR4 | CYR61 | DVL3 | E2F4 | ETS1 | H2AFZ | L1CAM | LRP1 |
| RAP1B | RPL30 | SLC25A5 | SPP1 | TAF12 | TBX19 | blank | β-actin |
| RAP1B | RPL30 | SLC25A5 | SPP1 | TAF12 | TBX19 | blank | β-actin |
| RAP1B | RPL30 | SLC25A5 | SPP1 | TAF12 | TBX19 | blank | β-actin |

FIG. 2

| Gene name | overexpression rate (%) | Gene name | overexpression rate (%) | Gene name | overexpression rate (%) |
|---|---|---|---|---|---|
| ATP2A2 | 83 | SLC25A5 | 74 | H2AFZ | 65 |
| CXCR4 | 81 | CALM2 | 75 | TBX19 | 64 |
| RAP1B | 89 | E2F4 | 78 | COL4A1 | 51 |
| ATP6V0B | 90 | SPP1 | 72 | L1CAM | 53 |
| CYR61 | 86 | CEBPB | 66 | CXCL11 | 54 |
| RPL30 | 92 | ETS1 | 68 | LRP1 | 57 |
| BMPR2 | 76 | TAF12 | 64 | Total Score | 58 |
| DVL3 | 79 | CLSTN1 | 68 | | |

| Cancer tissue | CAKM-1 | CAKM-2 | CAKWT-1 | CAKWT-2 |
|---|---|---|---|---|
| Array Image | | | | |
| result | +36 | +32 | -8 | -6 |

SEQUENCE LISTING

<160> NUMBER OF SEQ ID NOS: 23

<210> SEQ ID NO 1
<211> LENGTH: 50
<212> TYPE: DNA
<213> ORGANISM: Artificial sequence
<220> FEATURE:
<223> OTHER INFORMATION: Gene fragment from Homo sapiens

<400> SEQUENCE: 1
acccggactt tgaaggcgtg gattgtgcaa tctttgaatc cccatacccg         50

<210> SEQ ID NO 2
<211> LENGTH: 46
<212> TYPE: DNA
<213> ORGANISM: Artificial sequence
<220> FEATURE:
<223> OTHER INFORMATION: Gene fragment from Homo sapiens

<400> SEQUENCE: 2
catcggccat cggaactacc atgcaggcta ctccatgttt ggggct           46

<210> SEQ ID NO 3
<211> LENGTH: 48
<212> TYPE: DNA
<213> ORGANISM: Artificial sequence
<220> FEATURE:
<223> OTHER INFORMATION: Gene fragment from Homo sapiens

<400> SEQUENCE: 3
acaacatcgc cctgtggatg actgagtacc tgaaccggca cctgcaca         48

<210> SEQ ID NO 4
<211> LENGTH: 59
<212> TYPE: DNA
<213> ORGANISM: Artificial sequence
<220> FEATURE:
<223> OTHER INFORMATION: Gene fragment from Homo sapiens

<400> SEQUENCE: 4
gaagcattcc gtgtgtttga taaggatggc aatggctata ttagtgctgc agaacttcg     59

<210> SEQ ID NO 5
<211> LENGTH: 50
<212> TYPE: DNA
<213> ORGANISM: Artificial sequence
<220> FEATURE:
<223> OTHER INFORMATION: Gene fragment from Homo sapiens

<400> SEQUENCE: 5
ccgcctgcct ttaaatccat ggaagtggcc aacttctact acgaggcgga         50

<210> SEQ ID NO 6
<211> LENGTH: 50
<212> TYPE: DNA
<213> ORGANISM: Artificial sequence
<220> FEATURE:
<223> OTHER INFORMATION: Gene fragment from homo sapiens

<400> SEQUENCE: 6
tctctcctct ctcctcccca gagcaccccc tgccatcagg ggggttgaaa         50

<210> SEQ ID NO 7
<211> LENGTH: 50
<212> TYPE: DNA

```
<213> ORGANISM: Artificial sequence
<220> FEATURE:
<223> OTHER INFORMATION: Gene fragment from homo sapiens

<400> SEQUENCE: 7
gcaaatgtga ctgccatgga gtgaagggac aaaagggtga aagaggcctc                    50

<210> SEQ ID NO 8
<211> LENGTH: 50
<212> TYPE: DNA
<213> ORGANISM: Artificial sequence
<220> FEATURE:
<223> OTHER INFORMATION: Gene fragment from homo sapiens

<400> SEQUENCE: 8
gttcaaggct tccccatgtt caaaagagga cgctgtcttt gcataggccc                    50

<210> SEQ ID NO 9
<211> LENGTH: 52
<212> TYPE: DNA
<213> ORGANISM: Artificial sequence
<220> FEATURE:
<223> OTHER INFORMATION: Gene fragment from Homo sapiens

<400> SEQUENCE: 9
ccccatcctc tatgctttcc ttggagccaa atttaaaacc tctgcccagc ac                 52

<210> SEQ ID NO 10
<211> LENGTH: 50
<212> TYPE: DNA
<213> ORGANISM: Artificial sequence
<220> FEATURE:
<223> OTHER INFORMATION: Gene fragment from homo sapiens

<400> SEQUENCE: 10
cagcagcctg aaaaagggca agaaatgcag caagaccaag aaatcccccg                    50

<210> SEQ ID NO 11
<211> LENGTH: 50
<212> TYPE: DNA
<213> ORGANISM: Artificial sequence
<220> FEATURE:
<223> OTHER INFORMATION: Gene fragment from Homo sapiens

<400> SEQUENCE: 11
cgtcaccttg gcggacttta agggcgtttt gcagcgaccc agctataagt                    50

<210> SEQ ID NO 12
<211> LENGTH: 46
<212> TYPE: DNA
<213> ORGANISM: Artificial sequence
<220> FEATURE:
<223> OTHER INFORMATION: Gene fragment from homo sapiens

<400> SEQUENCE: 12
tgagatcaca gtgagtggcg gccctgggac tgatagcaag gacagt                        46

<210> SEQ ID NO 13
<211> LENGTH: 50
<212> TYPE: DNA
<213> ORGANISM: Artificial sequence
<220> FEATURE:
<223> OTHER INFORMATION: Gene fragment from homo sapiens

<400> SEQUENCE: 13
tggagcagcc agtcatcttt caacagcctg cagcgtgttc cctcctatga                    50
```

-continued

<210> SEQ ID NO 14
<211> LENGTH: 57
<212> TYPE: DNA
<213> ORGANISM: Artificial sequence
<220> FEATURE:
<223> OTHER INFORMATION: Gene fragment from homo sapiens

<400> SEQUENCE: 14
cgtggagatg aagaattgga ttctctcatc aaggctacaa ttgctggtgg tggtgtc    57

<210> SEQ ID NO 15
<211> LENGTH: 50
<212> TYPE: DNA
<213> ORGANISM: Artificial sequence
<220> FEATURE:
<223> OTHER INFORMATION: Gene fragment from Homo sapiens

<400> SEQUENCE: 15
ccttcctggt ggtgtccaac acgtccacct tcgtgcccta tgagatcaaa    50

<210> SEQ ID NO 16
<211> LENGTH: 49
<212> TYPE: DNA
<213> ORGANISM: Artificial sequence
<220> FEATURE:
<223> OTHER INFORMATION: Gene fragment from Homo sapiens

<400> SEQUENCE: 16
atgcctgtga aaacgaccag tatgggaagc cgggtggctg ctctgacat    49

<210> SEQ ID NO 17
<211> LENGTH: 65
<212> TYPE: DNA
<213> ORGANISM: Artificial sequence
<220> FEATURE:
<223> OTHER INFORMATION: Gene fragment from Homo sapiens

<400> SEQUENCE: 17
ggaagatgaa agagttgtag ggaaggaaca aggtcaaaat ctagcaagac aatggaacaa    60
ctgtg    65

<210> SEQ ID NO 18
<211> LENGTH: 51
<212> TYPE: DNA
<213> ORGANISM: Artificial sequence
<220> FEATURE:
<223> OTHER INFORMATION: Gene fragment from Homo sapiens

<400> SEQUENCE: 18
gctccaactc gttatgaaaa gtgggaagta cgtcctgggg tacaagcaga c    51

<210> SEQ ID NO 19
<211> LENGTH: 50
<212> TYPE: DNA
<213> ORGANISM: Artificial sequence
<220> FEATURE:
<223> OTHER INFORMATION: Gene fragment from Homo sapiens

<400> SEQUENCE: 19
tctgatggga ttaagggcct gtaccaaggc tttaacgtgt ctgtgcaggg    50

<210> SEQ ID NO 20
<211> LENGTH: 51
<212> TYPE: DNA
<213> ORGANISM: Artificial sequence
<220> FEATURE:

```
-continued

<223> OTHER INFORMATION: Gene fragment from Homo sapiens

<400> SEQUENCE: 20
gtggacagcc aggactccat tgactcgaac gactctgatg atgtagatga c          51

<210> SEQ ID NO 21
<211> LENGTH: 50
<212> TYPE: DNA
<213> ORGANISM: Artificial sequence
<220> FEATURE:
<223> OTHER INFORMATION: Gene fragment from Homo sapiens

<400> SEQUENCE: 21
cagcacccct ccacaaggct ccatggccaa tagtactgca gtggtaaaga             50

<210> SEQ ID NO 22
<211> LENGTH: 50
<212> TYPE: DNA
<213> ORGANISM: Artificial sequence
<220> FEATURE:
<223> OTHER INFORMATION: Gene fragment from Homo sapiens

<400> SEQUENCE: 22
tcatctgctc aatgtggtgg agagtgagct tcaggcaggg agggaaaaag             50

<210> SEQ ID NO 23
<211> LENGTH: 60
<212> TYPE: DNA
<213> ORGANISM: Artificial sequence
<220> FEATURE:
<223> OTHER INFORMATION: Gene fragment

<400> SEQUENCE: 23
tgcattgtta caggaagtcc cttgccatcc taaaagccac cccacttctc tctaaggaga  60
```

GENE CLUSTER DIAGNOSIS APPARATUS

TECHNICAL FIELD OF THE DISCLOSURE

The present disclosure relates to a diagnosis apparatus; more particularly, relates to providing a fast, accurate, sensitive and cheap WEnCA-Chipball platform for mass analysis and automatic operation while human error and time for diagnosis are both reduced.

DESCRIPTION OF THE RELATED ARTS

For analyzing gene overexpression, some techniques are used, including northern blotting, reverse transcription polymerase chain reaction (RT-PCR) and real-time PCR. Therein, northern blotting is complex and uses too much amount of samples. RT-PCR and real-time PCR are thus widely used for diagnosing single gene owing to their simple operations, like diagnosing hepatitis virus or infectious pathogen. However, most PCR has problem in pollution for false positive owing to over-sensitivity, like sprayed DNA. In the other hand, RT-PCR is recognized as semi-quantity; hence, effect on magnifying sequence is hard to control when different samples are compared. Furthermore, owing to annealing interference on binding primers, RT-PCR and real-time PCR are both used for diagnosing one single type of gene only, where, on diagnosing a gene cluster, operations of PCR related techniques are time-wasting, complicated and expensive.

A membrane array is used for diagnosing cancer to obtain expression level of multiple labeled primers of mRNA in peripheral blood. The expression level of the molecular marker is evaluated by RT-PCR with a nylon film. Through linear regression, a high inter-relationship is shown between them (r=0.979, P<0.0001). Besides, a weighted chemiluminescent membrane array (WCHMA) is used to analyze target therapeutic drug effect on K-ras in peripheral blood for a lung cancer patient.

Although the nylon film is often used, diagnosis specificity is hard to be enhanced for each gene is evaluated as equal on diagnosing a disease. Moreover, digoxigenin used in a colorimetric biochip platform is very expensive. Not to mention that genechip operation requires high technique skills. Hence, the prior arts do not fulfill all users' requests on actual use.

SUMMARY OF THE DISCLOSURE

The main purpose of the present disclosure is to provide a fast, accurate, sensitive and cheap WEnCA-Chipball platform.

The second purpose of the present disclosure is to provide an automatic diagnosis apparatus without using big centrifuge.

The third purpose of the present disclosure is to purify extracted mRNA with Poly-T magnetic balls for low background and high accuracy after reaction.

The fourth purpose of the present disclosure is to use biotin-avidin as enzyme and diaminobenzidine as reagent for high stability.

The fifth purpose of the present disclosure is use a weighted calculation with coordination of positive reaction curve for precise diagnosis.

To achieve the above purposes, the present disclosure is a gene cluster diagnosis apparatus, comprising a gene chip, a preprocessing unit, a hybridizing region, a color development region and an analyzing unit, where the gene chip has a target gene cluster comprising a plurality of target genes related to a cancer; where the target gene cluster, an internal control and a blank control are obtained in arrays with gene in triplicate on a nylon film to obtain a labeled specific sequence; where the preprocessing unit purifies mRNA obtained from a sample and labels the mRNA to obtain probes after reverse-transcribing the mRNA into cDNA; where the hybridizing region processes hybridization to the probes in the gene chip; where the color development region processes color development by applying diaminobenzidine (DAB) to the probes after the hybridization; where the analyzing unit has an analysis software and the analyzing unit has an image capturing mode and a data transferring mode; and where the analyzing unit has a procedure comprising steps of: capturing an image of the gene chip after the color development; processing an automatic analysis to the image of the gene chip; processing a gene weighted calculation to a plurality of detection values obtained after the automatic analysis; and multiplying a number of gene spots having positive reaction with weighted values for the gene spots to obtain a total score. Accordingly, a novel gene cluster diagnosis apparatus is obtained.

BRIEF DESCRIPTIONS OF THE DRAWINGS

The present disclosure will be better understood from the following detailed description of the preferred embodiment according to the present disclosure, taken in conjunction with the accompanying drawings, in which.

DESCRIPTION OF THE PREFERRED EMBODIMENT

The following description of the preferred embodiment is provided to understand the features and the structures of the present disclosure.

Figure 1:
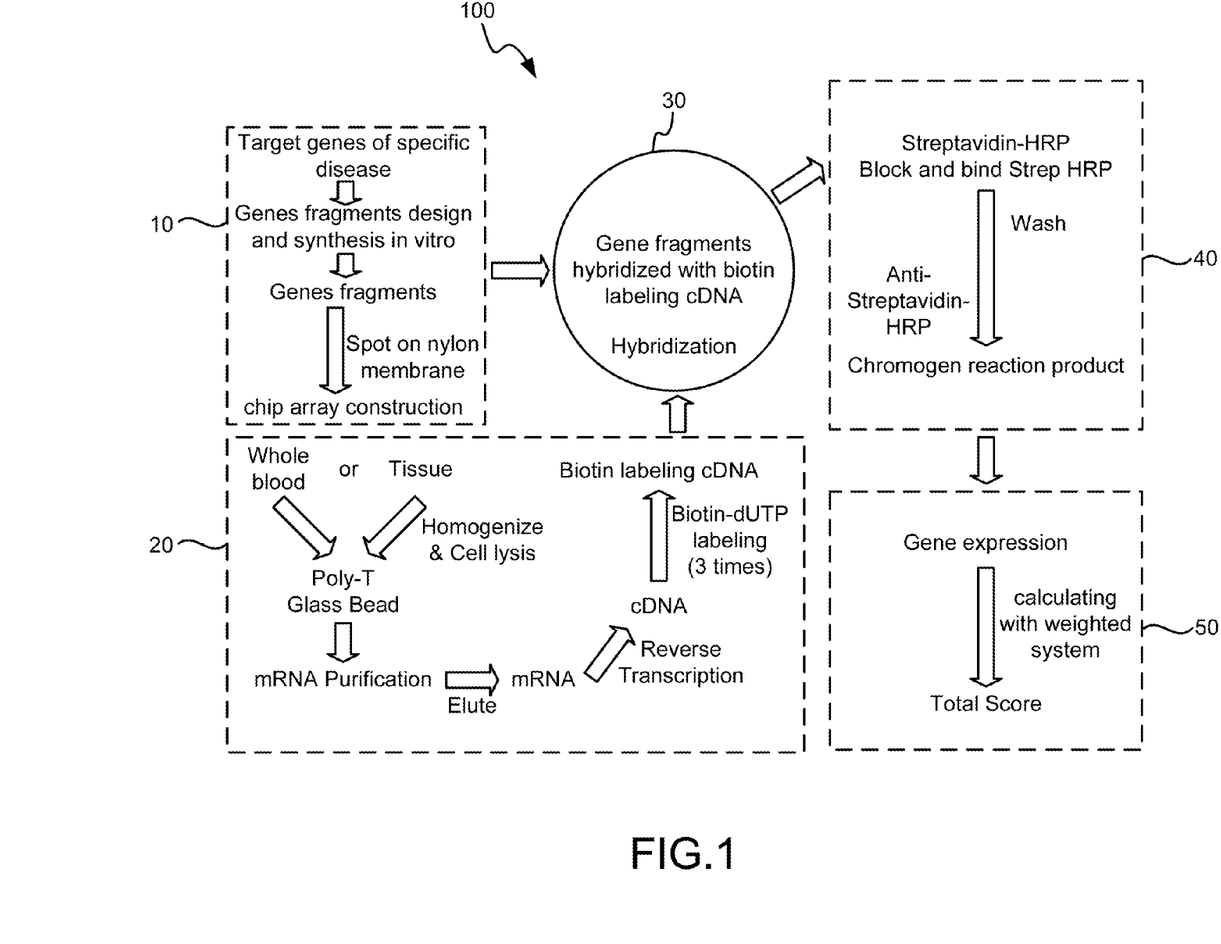
FIG. 1 is the view showing the preferred embodiment according to the present disclosure.
Figure 2:
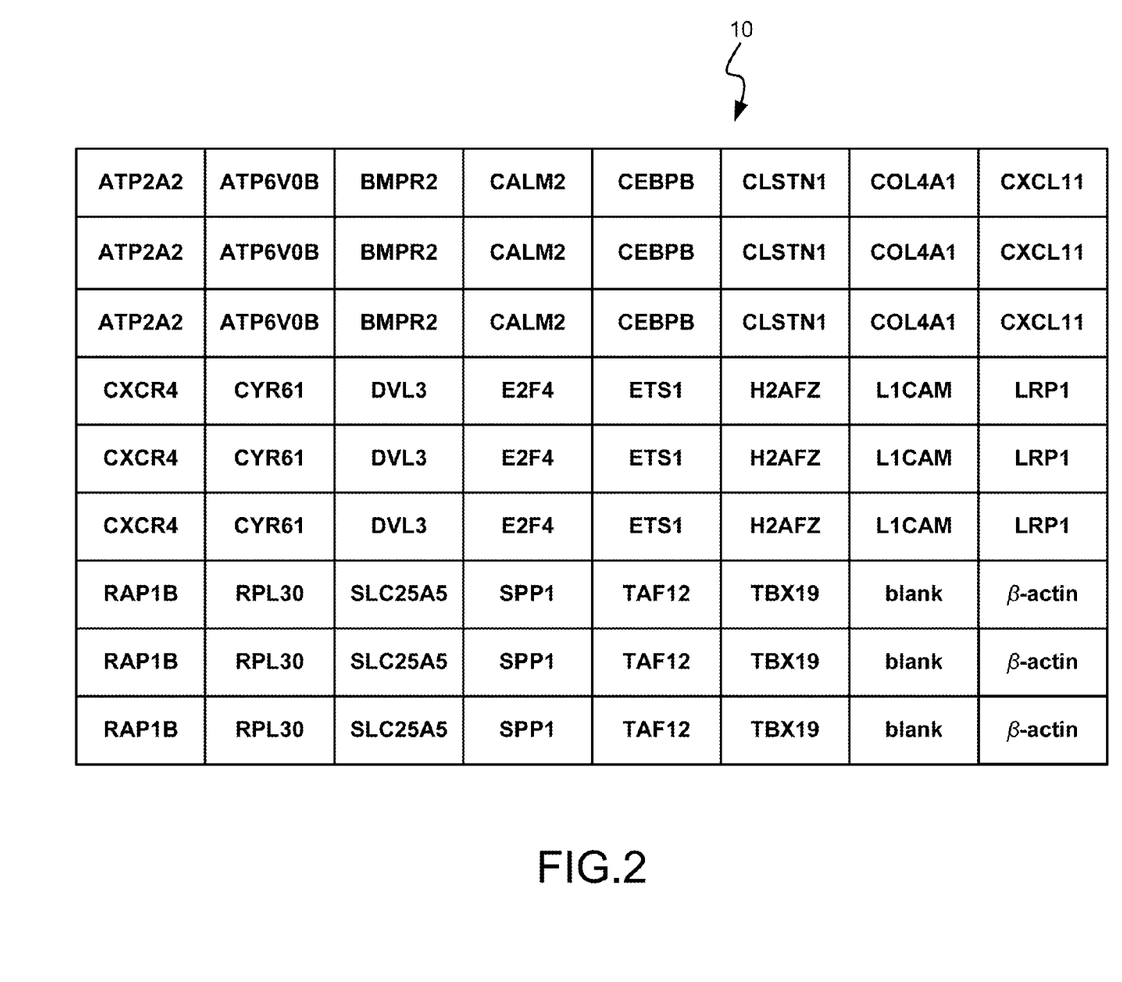
FIG. 2 is the view showing the arrangement of the genes in the gene chip, including ATP2A2 (SEQ ID NO:1), ATP6VOB (SEQ ID NO:2), BMPR2 (SEQ ID NO:3), CALM2 (SEQ ID NO:4), CEBPB (SEQ ID NO:5), CLSTN1 (SEQ ID NO:6), COL4A1 (SEQ ID NO:7), CXCL11 (SEQ ID NO:8), CXCR4 (SEQ ID NO:9), CYR61 (SEQ ID NO:10), DVL3 (SEQ ID NO:11), E2F4 (SEQ ID NO:12), ETS1 (SEQ ID NO:13), H2AFZ (SEQ ID NO:14), L1CAM (SEQ ID NO:15), LRP1 (SEQ ID NO:16), RAP1B (SEQ ID NO:17), RPL30 (SEQ ID NO:18), SLC25A5 (SEQ ID NO:19), SPP1 (SEQ ID NO:20), TAF12 (SEQ ID NO:21), TBX19 (SEQ ID NO:21), and β-actin (SEQ ID NO:23)

Please refer to FIG. 1 and FIG. 2, which are a view showing a preferred embodiment according to the present disclosure;

and a view showing arrangement of genes in a gene chip. As shown in the figures, the present disclosure is a gene cluster diagnosis apparatus 100, comprising a gene chip 10, a preprocessing unit 20, a hybridizing region 30, a color development region 40 and an analyzing unit 50.

The gene chip 10 has a labeled specific sequence for disease diagnosis, evaluating drug effect or filtering hereditary disease gene.

The preprocessing unit 20 breaks cells in a sample after added with a lysis buffer for extracting mRNA. Magnetic particles are added to be combined with RNA; and, RNA is separated from the lysis buffer by washing for eluting mRNA with the magnetic particles. Then, the mRNA thus purified is reverse-transcribed into cDNA to be labeled as probes by enzyme. Therein, the sample can be blood, body fluid, cultured cells or tissue cells.

The hybridizing region 30 is used to process hybridization in the gene chip 10 with the probes and to wash out un-reacted probes from the chip.

The development region 40 processes color development by applying diaminobenzidine (DAB) to the probes after the hybridization.

The analyzing unit 50 is built-in with an analysis software and has an image capturing mode and a data transferring mode. An image of the gene chip 10 obtained after the color development is taken under the image capturing mode; and, the image is processed through an automatic analysis with the analysis software. Result values obtained after the analysis are processed through a gene weighted calculation, where each gene is weighted individually according to its importance on causing disease or resistance; and numbers of gene spots having positive reaction are then multiplied with the weighted values of the gene spots for figuring out a total score.

Thus, a novel gene cluster diagnosis apparatus 100 is obtained.

On using the present disclosure, each target gene in the chip is given a weighted value (e.g. lung cancer ref) with biotin-avidin used for building a weighted enzymatic chip array (WEnCA) platform. Since the platform can combined with a fluidic control platform easily for an automatic operation, diagnosis time and error from human labor can be greatly reduced for merchandising the gene cluster diagnosis apparatus.

To confirm the effect of the present disclosure, peripheral blood of 100 colorectal cancer (CRC) clinical patients are obtained. The gene chip 10 built for activated K-ras detection is used to diagnose overexpression of K-ras pathway related genes by a nylon film and the present disclosure 100 (i.e. WEnCA-chipball) for comparing differences in sensitivity, specificity and accuracy where operation time and required cost for clinical application are greatly reduced.

In FIG. 2, the gene chip 10 built for activated K-ras detection obtains a colorectal cancer related target gene cluster, which has 22 target genes. The target gene cluster, an internal control and a blank control are dotted in arrays with the gene in triplicate on the nylon film to form a labeled specific sequence. Therein, the target gene cluster comprises ATP2A2 (SEQ ID NO:1), ATP6V0B (SEQ ID NO:2), CXCR4 (SEQ ID NO:9), CYR61 (SEQ ID NO:10), RAP1B (SEQ ID NO:17), RPL30 (SEQ ID NO:18), BMPR2 (SEQ ID NO:3), CALM2 (SEQ ID NO:4), DVL3 (SEQ ID NO:11), E2F4 (SEQ ID NO:12), SLC25A5 (SEQ ID NO:19), SPP1 (SEQ ID NO:20), CEBPB (SEQ ID NO:5), CLSTN1 (SEQ ID NO:6), ETS1 (SEQ ID NO:13), H2AFZ (SEQ ID NO:14), TAF12 (SEQ ID NO:21), TBX19 (SEQ ID NO:21), COL4A1 (SEQ ID NO:7), CXCL11 (SEQ ID NO:8), L1CAM (SEQ ID NO:15), and LRP1 (SEQ ID NO:16); and the internal control is β-actin (SEQ ID NO:23).

Figure 3A:
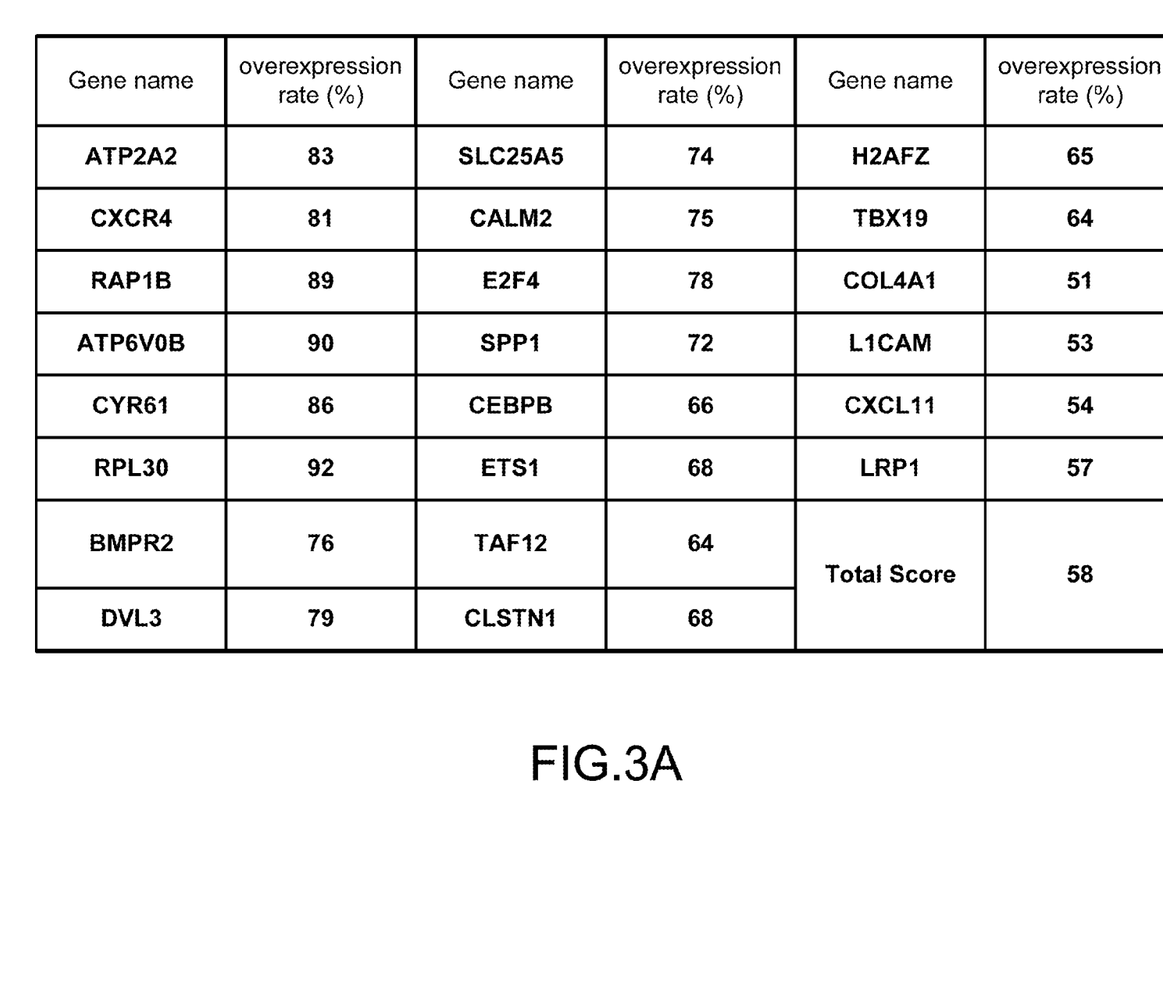
FIG. 3A is the view showing the overexpression ratios of genes in the target gene cluster, including ATP2A2 (SEQ ID NO:1), ATP6V0B (SEQ ID NO:2), BMPR2 (SEQ ID NO:3), CALM2 (SEQ ID NO:4), CEBPB (SEQ ID NO:5), CLSTN1 (SEQ ID NO:6), COL4A1 (SEQ ID NO:7), CXCL11 (SEQ ID NO:8), CXCR4 (SEQ ID NO:9), CYR61 (SEQ ID NO:10), DVL3 (SEQ ID NO:11), E2F4 (SEQ ID NO:12), ETS1 (SEQ ID NO:13), H2AFZ (SEQ ID NO:14), L1CAM (SEQ ID NO:15), LRP1 (SEQ ID NO:16), RAP1B (SEQ ID NO:17), RPL30 (SEQ ID NO:18), SLC25A5 (SEQ ID NO:19), SPP1 (SEQ ID NO:20), TAF12 (SEQ ID NO:21), TBX19 (SEQ ID NO:21)
Figure 3B:
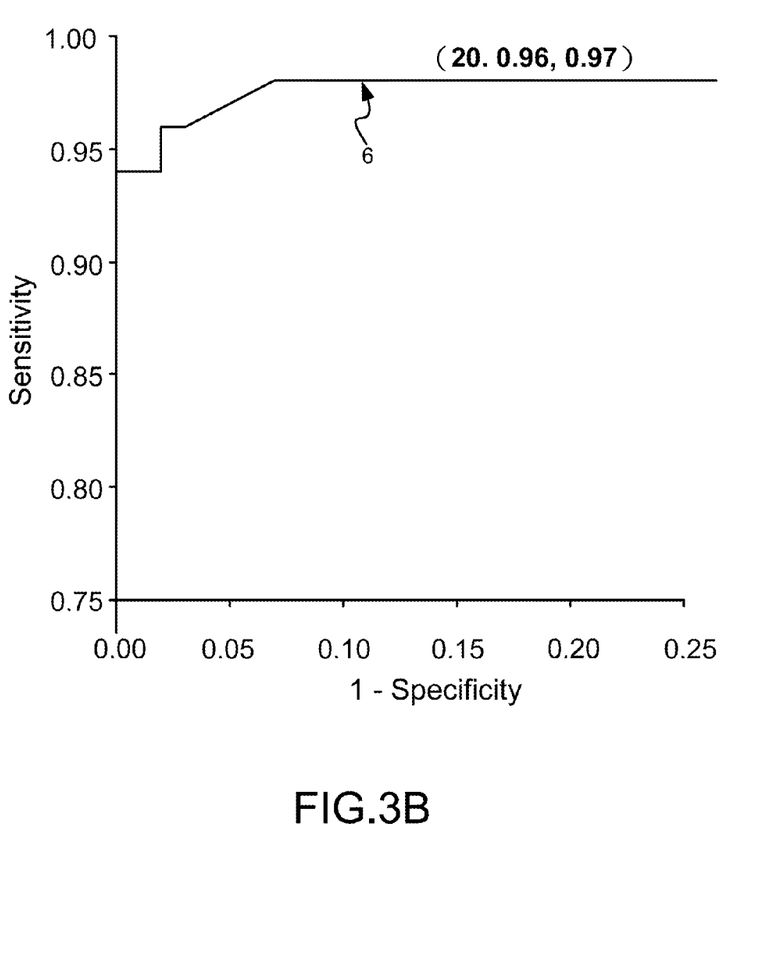
FIG. 3B is the view showing the ROC curve.
Figure 4:
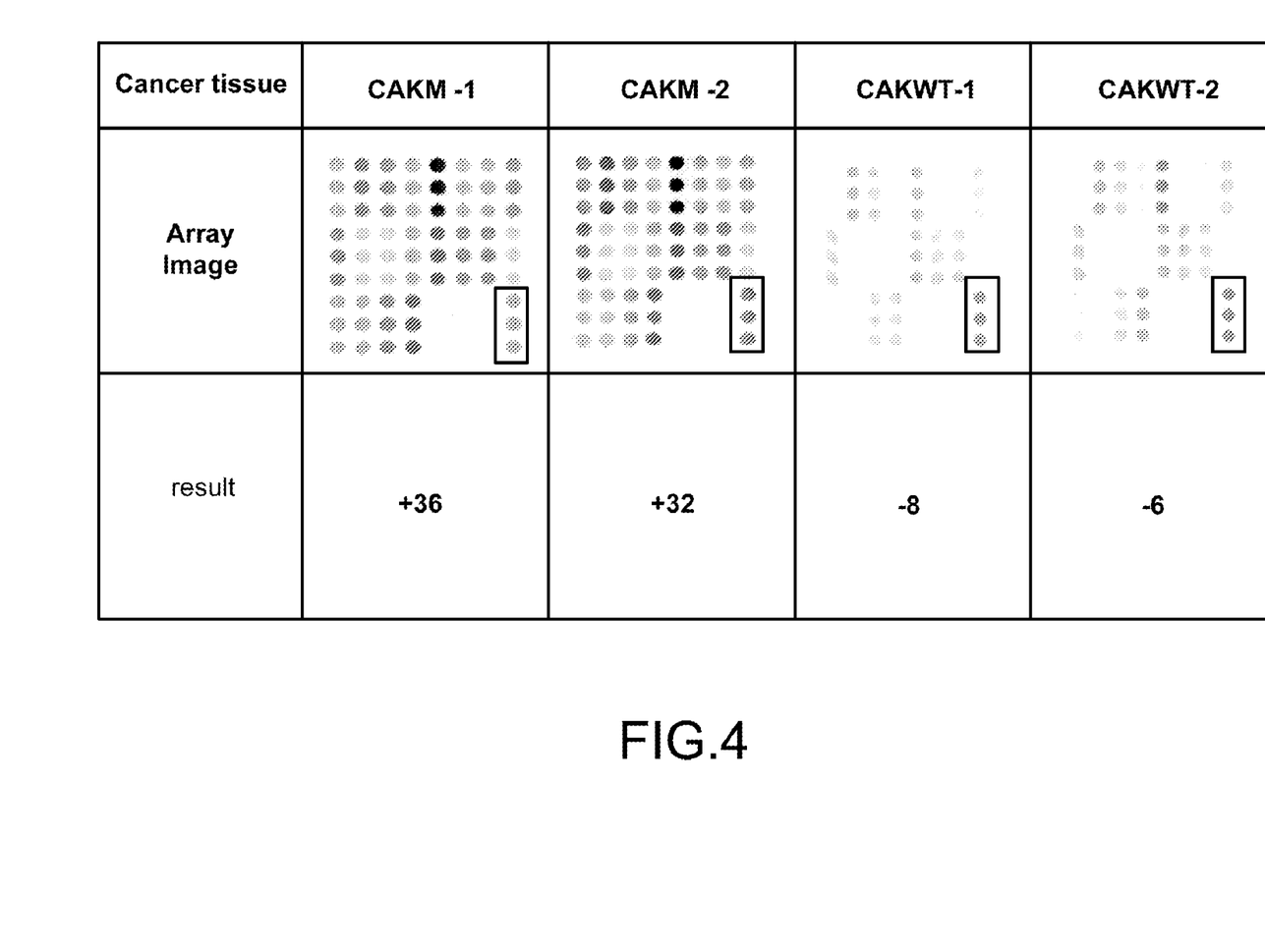
FIG. 4 is the view showing the image of the chip after the cancer tissue reaction.

Please further refer to FIG. 3A and FIG. 3B, which are a view showing overexpression ratios of genes in a target gene cluster; and a view showing an ROC curve. As shown in the figures, for analyzing reaction of a weighted chemiluminescent membrane array, overexpression ratios of 22 gene spots in 100 K-ras cancer tissues are diagnosed. In FIG. 3A, four weighted values are given to the gene spots having positive reaction, where 4 are given for a number of the gene spots more than 80; 3 for a number between 70 and 80; 2 for a number between 60 and 70; and 1 for a number between 50 and 60. The numbers of the gene spots having positive reaction are multiplied with their corresponding weighted values to figure out a total value of the chip. Through biological statistic analysis, a receiver operating characteristic curve (ROC Curve) is obtained in FIG. 3B. The curve shows that, when a cutoff value is set as 20 for the positive reaction in the chip, 96% sensitivity and 97% specificity can be achieved Please further refer to FIG. 4, which is a view showing an image of a chip after a cancer tissue reaction. As shown in the figure, a cancer tissue having K-ras mutation is named as CAKM; and a cancer tissue having wild type K-ras, CAKWT. Therein, the total values for CAKM-1 and CAKM-2 are respectively 36 and 32, which are both bigger than 20 and thus are positive; and, the total values for CAKWT-1 and CAKWT-2 are respectively 8 and 6, which are both smaller than 20 and thus are negative.

Figure 5:
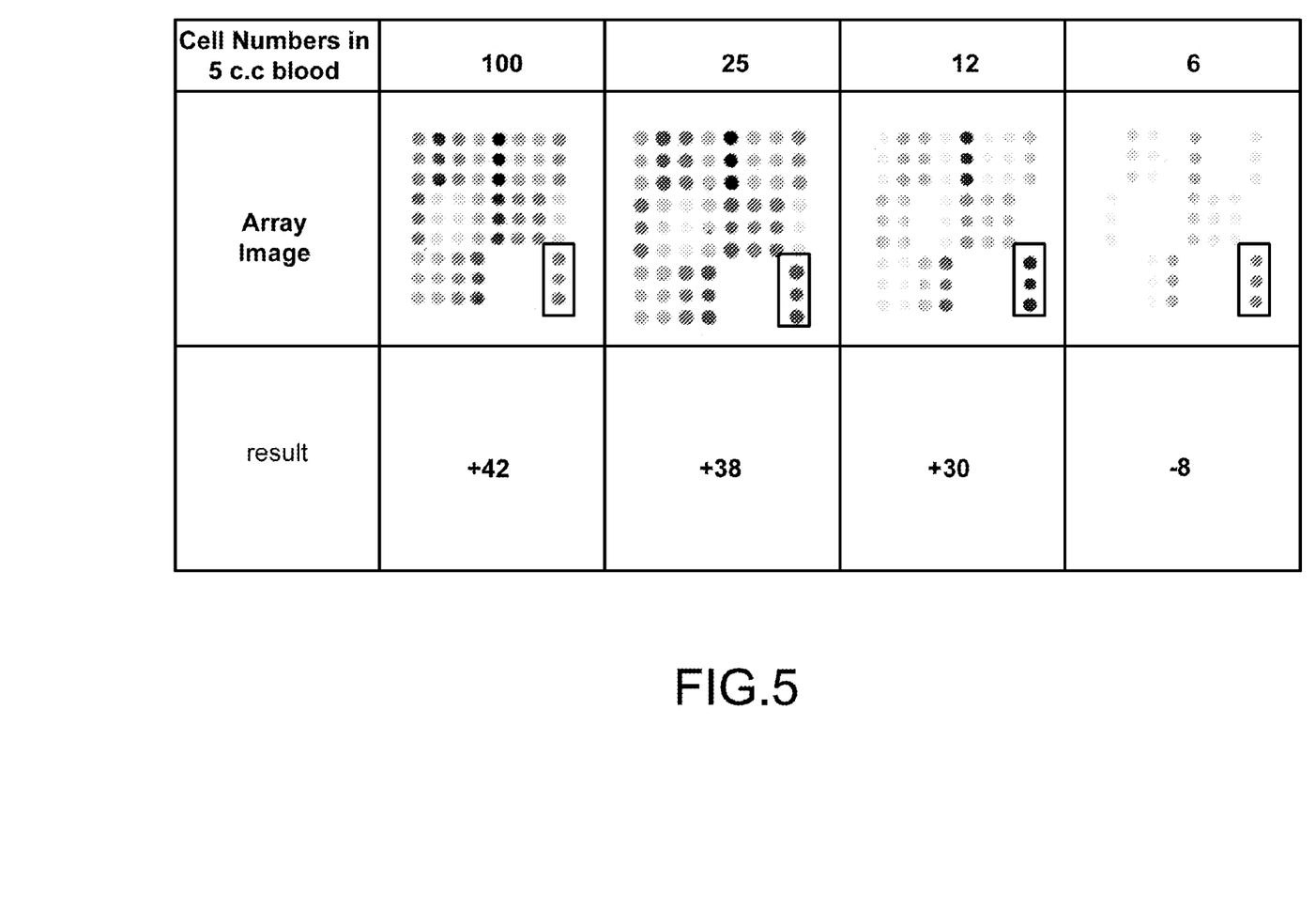
FIG. 5 is the view showing the analysis result of the detection limitation.

Please refer to FIG. 5, which is a view showing an analysis result of a detection limitation. As shown in the figure, on analyzing detection limitation, 5 C.C full blood is added to 100, 50, 23, 12 cancer cells having activated mutant K-ras gene separately. The total values obtained after the analysis are all bigger than 20, except for one added into 6 cancer cells with a value 8 smaller than 20 obtained. A detection limitation is thus figured out at about 2.4 cell/C.C blood.

Figure 6:
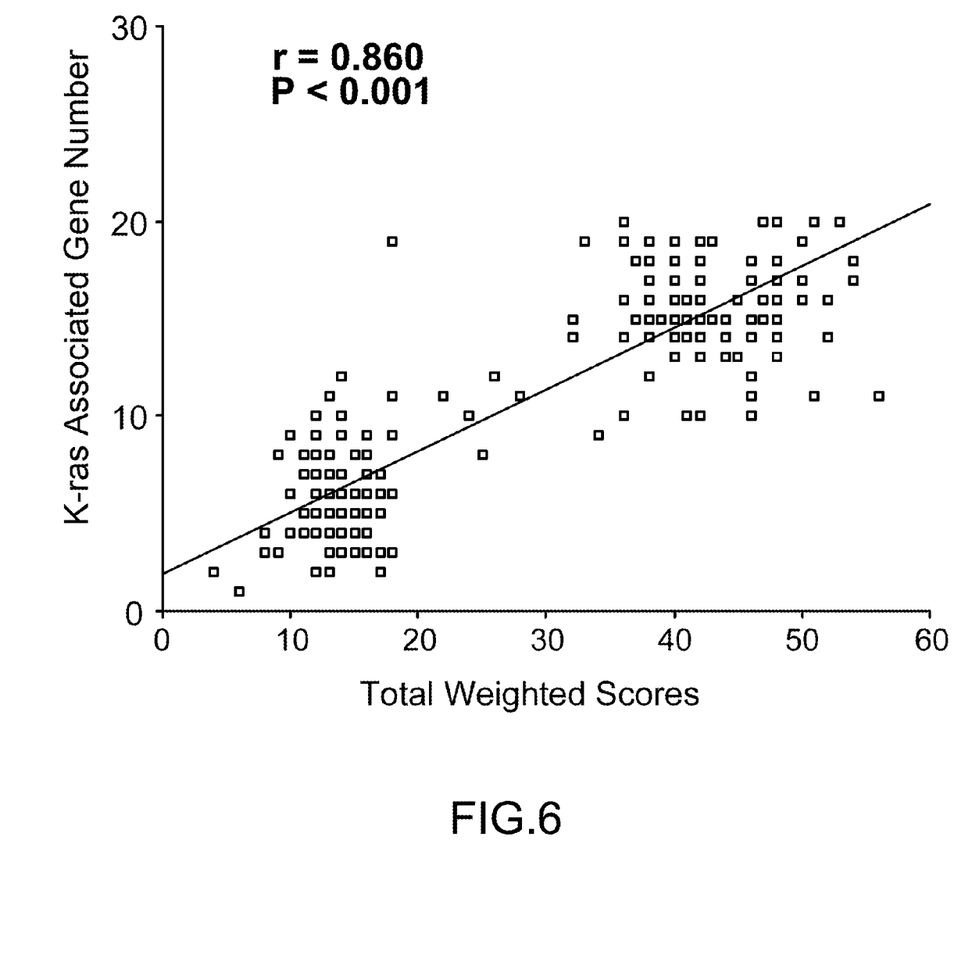
FIG. 6 is the view showing the linear regression analysis.

Please further refer to FIG. 6, which is a view showing a linear regression analysis. As shown in the figure, on analyzing consistency of the above results shown in FIG. 5, a linear regression analysis is used, and an r value is obtained as 0.86, which shows an obvious consistency in statics.

Hence, the present disclosure provides a fast, accurate, sensitive and cheap WEnCA-Chipball platform for mass analysis and automatic operation. The present disclosure diagnoses bio-samples rapidly without using big centrifuge and thus is easily operated, where Poly-T magnetic balls are used to purify extracted mRNA for reducing background and obtaining high accuracy. Besides, the present disclosure uses biotin-avidin for low cost and high stability. Furthermore, a weighted calculation is used with coordination of ROC curve for precise diagnosis. Hence, the present disclosure has high sensitivity, specificity and accuracy on clinics and time for diagnosis is greatly reduced while human error is reduced as well.

To sum up, the present disclosure is a gene cluster diagnosis apparatus, where a fast, accurate, sensitive and cheap WEnCA-Chipball platform is provided for mass analysis and automatic operation.

The preferred embodiment herein disclosed is not intended to unnecessarily limit the scope of the disclosure. Therefore, simple modifications or variations belonging to the equivalent of the scope of the claims and the instructions disclosed herein for a patent are all within the scope of the present disclosure.

What is claimed is:

1. A weighted gene cluster diagnosis apparatus, comprising
   a gene chip, said gene chip comprising a target gene cluster, said target gene cluster comprising a plurality of target genes related to a cancer, wherein said target gene cluster, an internal control and a blank control are obtained in arrays with each gene in triplicate on a nylon film to obtain a labeled specific sequence;
   a preprocessing unit, said preprocessing unit purifying mRNA obtained from a sample and labeling said mRNA to obtain probes after reverse-transcribing said mRNA into cDNA;
   a hybridizing region, said hybridizing region processing hybridization to said probes in said gene chip;
   a color development region, said color development region processing color development by applying diaminobenzidine (DAB) to said probes after said hybridization; and
   an analyzing unit, said analyzing unit having an analysis software, said analyzing unit having an image capturing mode and a data transferring mode, said analyzing unit having a procedure comprising steps of:
   capturing an image of said gene chip after said color development;
   processing an automatic analysis to said image of said gene chip;
   processing a gene weighted calculation to a plurality of detection values obtained after said automatic analysis; and
   multiplying a number of gene spots having positive reaction with weighted values for said gene spots to obtain a total score.

2. The apparatus according to claim 1, wherein said gene chip has a function selected from a group consisting of building complete disease diagnosis, evaluating drug effect and filtering hereditary disease gene.

3. The apparatus according to claim 1, wherein said target genes having positive reaction obtains said detection values and said detection value is a weighted value selected from a group consisting of:
   (a) 4 for a number of said gene spots of said target gene more than 80;
   (b) 3 for a number of said gene spots of said target gene between 70 and 80;
   (c) 2 for a number of said gene spots of said target gene between 60 and 70; and
   (d) 1 for a number of said gene spots of said target gene between 50 and 60.

4. The apparatus according to claim 1, wherein said analyzing unit obtains a positive cutoff value of said gene chip based on a receiver operating characteristic curve (ROC curve).

5. The apparatus according to claim 4, wherein said positive cutoff value is 20±20%.

6. The apparatus according to claim 1, wherein said apparatus has a detection limitation at 2.4±20% cells/C.C blood.

7. The apparatus according to claim 1, wherein said target gene cluster comprises ATP2A2 (SEQ ID NO:1), ATP6V0B (SEQ ID NO:2), CXCR4 (SEQ ID NO:9), CYR61 (SEQ ID NO:10), RAP1 (SEQ ID NO:17), RPL30 (SEQ ID NO:18), BMPR2 (SEQ ID NO:3), CALM2 (SEQ ID NO:4), DVL3 (SEQ ID NO:11), E2F4 (SEQ ID NO:12), SLC25A5 (SEQ ID NO:19), SPP1 (SEQ ID NO:20), CEBPB (SEQ ID NO:5), CLSTN1 (SEQ ID NO:6), ETS1 (SEQ ID NO:13), H2AFZ (SEQ ID NO:14), TAF2 (SEQ ID NO:21), TBX19 (SEQ ID NO:21), COL4A1 (SEQ ID NO:7), CXCL11 (SEQ ID NO:8), L1CAM (SEQ ID NO:15), and LRP1 (SEQ ID NO:16).

8. The apparatus according to claim 1, wherein said internal control is β-actin (SEQ ID NO:23).

9. The apparatus according to claim 1, wherein said sample is selected from a group consisting of blood, body fluid, cultured cells and tissue cells.

* * * * *